(12) United States Patent
Ouchi

(10) Patent No.: US 6,613,068 B2
(45) Date of Patent: Sep. 2, 2003

(54) ENDOSCOPIC TREATMENT INSTRUMENT

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 44 days.

(21) Appl. No.: 09/799,069

(22) Filed: Mar. 6, 2001

(65) Prior Publication Data

US 2001/0021860 A1 Sep. 13, 2001

(30) Foreign Application Priority Data

| Mar. 7, 2000 | (JP) | P2000-061309 |
| May 31, 2000 | (JP) | P2000-162131 |
| May 16, 2000 | (JP) | P2000-142703 |

(51) Int. Cl.$^7$ ............................................. A61B 17/28
(52) U.S. Cl. ........................ 606/205; 606/170; 606/174
(58) Field of Search ................................ 606/167, 170, 606/174, 205, 206, 207, 208

(56) References Cited

U.S. PATENT DOCUMENTS

| 4,200,111 A | | 4/1980 | Harris | |
| 5,133,727 A | * | 7/1992 | Bales et al. | 606/170 |
| 5,141,519 A | * | 8/1992 | Smith et al. | |
| 5,228,451 A | * | 7/1993 | Bales et al. | 600/564 |
| 5,331,971 A | * | 7/1994 | Bales et al. | |
| 5,419,339 A | * | 5/1995 | Palmer | 600/564 |
| 5,507,296 A | * | 4/1996 | Bales et al. | |
| 5,553,624 A | * | 9/1996 | Francese et al. | |
| 5,722,421 A | * | 3/1998 | Francese et al. | 600/564 |
| 5,752,972 A | * | 5/1998 | Hoogeboom | 606/174 |
| 5,819,738 A | * | 10/1998 | Slater | 600/564 |
| 5,908,437 A | * | 6/1999 | Asano et al. | 606/205 |
| 6,106,543 A | * | 8/2000 | Esser | 606/205 |
| 6,299,630 B1 | * | 10/2001 | Yamamoto | 606/170 |

FOREIGN PATENT DOCUMENTS

| DE | 19948387 | | 5/2000 |
| EP | 491890 | * | 7/1992 |
| JP | 11178829 | * | 7/1999 |
| JP | 2000-175928 A | * | 6/2000 |

* cited by examiner

Primary Examiner—Gary L. Welch
Assistant Examiner—Shaun R Hurley
(74) Attorney, Agent, or Firm—Greenblum & Bernstein, P.L.C.

(57) ABSTRACT

In an endsocopic treatment instrument, a distal end of a manipulating wire extending from the distal end of a sheath is provided with a large-diameter portion that is large enough to be incapable of passing through an engagement through-hole in the plate portion of an actuating member. The manipulating wire is passed through the engagement hole until the large-diameter portion contacts one end of the engagement hole, and is bent back toward the distal end of the sheath at the other end of the engagement hole.

18 Claims, 15 Drawing Sheets

ENDOSCOPIC TREATMENT INSTRUMENT

BACKGROUND OF THE INVENTION

This invention relates to a coupling portion for the manipulating wire of an endoscopic treatment instrument which is typically used to perform medical treatments in body cavities and which is adapted to be passed through a treatment instrument insertion channel in an endoscope.

Many of the endoscopic treatment instruments known in the art are designed such that distal end actuating members provided at the distal end are driven to operate by means of a manipulating wire that is remotely manipulated to move back and forth. Taking the case of endoscopic biopsy forceps, the manipulating wire is brought into engagement with engagement through-holes in the plate portions of the distal end actuating members by passing the distal end of the wire through the holes. While many versions of this technology have been known, Unexamined Published Japanese Patent Application (kokai) No. 178829/1999 proposes that the distal end of a manipulating wire be formed as a continuous loop and passed through engagement holes formed in the distal end actuating members. In the proposal made by European Patent No. 491890, a manipulating wire 81 passed through an engagement hole 83 is bent in two positions, one before and the other after the hole 83.

However, both proposals have their own disadvantages. In the first case, the distal end of the manipulating wire as passed through the engagement hole has to be formed in a continuous loop and this involves considerable difficulty in working and assembling operations, thus rendering the proposal a practically infeasible idea. In the second case, the manipulating wire 81 is simply bent both before and after the engagement hole 83; hence, if a strong external force is exerted on the distal end actuating members or if a strong pulling force is applied to the manipulating wire 81, the bent portions of the wire 81 stretch out and become straight enough that the wire 81 may slip out of the engagement hole 83.

Endoscopic treatment instruments such as endoscopic forceps mentioned above suffer from a further problem. The endoscopic forceps generally have a pair of forceps sections coupled integrally to associated drive levers (i.e. the distal end actuating members) and each combination of a forceps section and the associated drive lever is supported in the distal end portion of a sheath such that the forceps section and the drive lever are pivotal on a support shaft provided near the boundary. A manipulating wire is passed through the sheath and by manipulating it to move back and forth along the longitudinal axis, each forceps section and the associated drive lever pivot on the support shaft to drive the forceps sections such that they open and close like a bird's beak.

In modern endoscopic forceps designed for simpler construction, the manipulating wire consists of two wires that are arranged side by side within the sheath and each of which is directly coupled at the distal end to the drive lever formed integral with an associated forceps section.

The problem with this design is that if two wires are simply arranged side by side, the pair of forceps sections are not synchronized in opening and closing motions and they just swing not to conform with the operator's intention. To deal with this situation, the manipulating wire is entirely covered with a flexible heat-shrinking tube or the like in areas other than the distal end and its nearby portion, and the two wires are bundled to ensure that their distal end portions can move back and forth simultaneously.

However, covering the manipulating wire with a tube or the like results in increasing the thickness of the sheath by a corresponding amount and this has caused disadvantages such as applicability being limited to endoscopes having a thick enough forceps channel.

SUMMARY OF THE INVENTION

The present invention has been accomplished under these circumstances.

An object of the present invention is to provide an endoscopic treatment instrument of such a type that a manipulating wire is brought into engagement with engagement through-holes in the plate portions of distal end actuating members by passing the distal end of the wire through the holes and which can be worked and assembled in a sufficiently simple manner to feature high practical feasibility while exhibiting sufficient strength to prevent the manipulating wire from coming out of engagement with the engagement holes.

Another object of the present invention is to provide an endoscopic treatment instrument of such a type that two wires are directly coupled to respective drive levers to construct a manipulating wire and which allows a pair of forceps sections to open and close by equal degrees without increasing the diameter of the sheath.

Still another object of the present invention is to provide an endoscopic treatment instrument of such a type that the distal ends of wires are directly coupled to drive levers held pivotal in a slit and which can be operated satisfactorily for an adequate period without having the distal ends of the wires get stuck at the throat of the slit.

The present invention is characterized in that the distal end of the manipulating wire extending from the distal end of the sheath is provided with a large-diameter portion that is large enough to be incapable of passing through an engagement hole in the plate portion of the distal end actuating member.

The present invention is also characterized in that the manipulating wire as passed through the engagement hole until the large-diameter portion contacts an end portion of the engagement hole is bent back toward the distal end of the sheath at the other end of the engagement hole.

This design offers high practical feasibility since the structure that brings the manipulating wire into engagement with the distal end actuating member can be realized by simple working and assembling operations. In addition, the structure has a sufficient strength against the loss of engagement.

The present invention is also characterized in that an endoscopic forceps has two wires arranged side by side within a sheath to construct a manipulating wire, with the distal end of each wire being coupled to an associated drive lever (actuating member), and the two wires are twisted together within the sheath in the neighborhood or vicinity of its distal end.

Because of this design, the forceps sections formed integral with the drive levers can be opened and closed by equal degrees so that they accurately move as desired. In addition, this can be achieved without increasing the diameter of the sheath and, hence, the endoscopic forceps of the invention finds extensive use if it is passed through endoscopes that have built-in forceps channels of ordinary diameters.

The present invention is also characterized in that the surface of each of two drive levers (actuating members) which contacts the inner sidewall of a slit in the area closer to the rear end is skived in such a way as to create a gap or space with the inner sidewall of the slit and a wire extending from the tip of a sheath is pulled into the gap and coupled to the associated drive lever.

As a result, the end of each wire is located in a wide space whose width is one half the width of the slit and even if it deforms to spread somewhat, the wires will not get stuck at the throat of the slit and allow the forceps cups to be opened and closed in positive movements.

An endoscopic treatment instrument according to a preferred embodiment comprises:

a sheath having a longitudinal axis;

a manipulating wire passed through the sheath and movable back and forth along the longitudinal axis;

a distal end actuating member disposed at a distal end of the sheath and driven by the manipulating wire;

an engagement hole provided to a plate portion of the distal end actuating member; and a large-diameter portion that is provided to a distal end of the manipulating wire and that is large enough to be incapable of passing through the engagement hole, wherein the manipulating wire as passed through the engagement hole until the large-diameter portion contacts one end portion of the engagement hole is bent back toward the distal end of said sheath at the other end of the engagement hole.

The large-diameter portion may be formed by expanding the distal end of the manipulating wire and hardening the distal end thus expanded. In this case, the large-diameter portion may be formed by expanding the distal end of the manipulating wire, melting the thus expanded distal end and then hardening the thus molten distal end.

Alternatively, the large-diameter portion may be formed by fastening a spherical piece to the distal end of the manipulating wire, or by fastening a flange member to the distal end of the manipulating wire.

The manipulating wire may be twisted with another manipulating wire at least in the vicinity of the distal end of the distal end of the sheath.

The one end of the engagement hole is preferably located closer to the longitudinal axis of the sheath than the other end of the engagement hole is located. In this case, the other end of the engagement hole is preferably spaced from an inner sidewall of the slit provided in a support frame supporting the distal end actuating member.

An endoscopic treatment instrument according to another preferred embodiment comprises:

a sheath having a longitudinal axis;

a pair of manipulating wires passed through the sheath and movable back and forth along the longitudinal axis;

a pair of distal end actuating members disposed at a distal end of the sheath and connected respectively to the manipulating wires;

wherein the manipulating wires are twisted with each other within the sheath at least in the vicinity of the distal end of the sheath.

The manipulating wires may be twisted with each other only in the vicinity of the distal end of the sheath, or otherwise may be twisted with each other substantially entirely from the vicinity of the distal end of the sheath to a basal end of the sheath.

In the latter case, it is preferable that a pitch on which the manipulating wires are twisted is smaller in a foremost end portion of a twist area than in other areas.

The endoscopic treatment instrument may further comprise a support frame having a slit and movably supporting the distal end actuating members, and each of the distal end actuating members may have a skived portion at a rear end portion to define a space from an inner side wall of the slit, and a part of each manipulating wire, which extends from a corresponding distal end actuating member to the distal end of the sheath may be located within a corresponding space.

An endoscopic treatment instrument according to yet another preferred embodiment comprises:

a sheath-having a longitudinal axis;

a manipulating wire passed through the sheath and movable back and forth along the longitudinal axis;

a distal end actuating member disposed at a distal end of the sheath and driven by the manipulating wire;

a support frame movably supporting the distal end actuating member, and having a slit defining an inner sidewall; and a skived portion provided to a rear end of the actuating member to define a space from the inner side wall, wherein the manipulating wire is passed through the space from the distal end of the sheath, and then connected to the actuating member.

The present disclosure relates to the subject matter contained in Japanese patent application Nos. Hei. 2000-61309 (filed on Mar. 7, 2000), 2000-142703 (filed on May 16, 2000) and 2000-162131 (filed on May 31, 2000), which are expressly incorporated herein by reference in their entireties.

DESCRIPTION OF THE PREFERRED EMBODIMENT

Several examples of the invention are now described with reference to the accompanying drawings.

Figure 2:
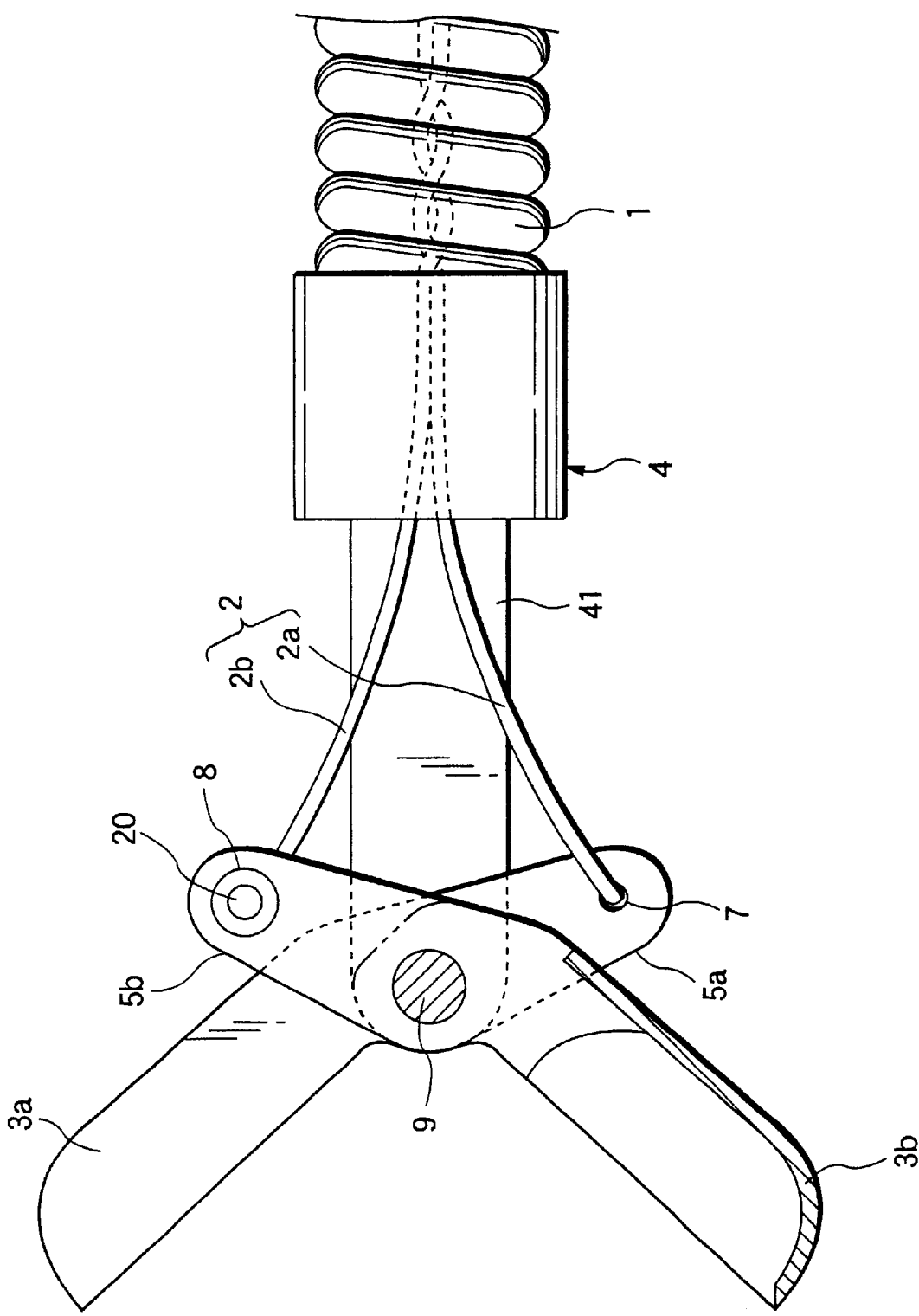
FIG. 2 is a side view showing in partial section the distal end portion of the endoscopic biopsy forceps according to the first example of the invention.

FIG. 2 shows an endoscopic biopsy forceps. It comprises a flexible sheath 1 that is to be inserted into or removed from an endoscopic treatment instrument insertion channel (not shown) and which is in the form of a coil pipe typically made of a stainless steel wire that is wound in close turns of a specified diameter.

A manipulating wire 2 extends through the entire length of the flexible sheath 1 in such a way that it can be moved back and forth along the longitudinal axis. The manipulating wire 2 is constructed by wires 2a and 2b each typically consisting of fine stainless steel wires stranded together.

Coupled at the basal end of the sheath 1 (at the right of FIG. 2) is a manipulating section 10 (see FIG. 16) for moving the manipulating wire 2 back and forth. A distal end support member 4 is securely coupled to the distal end of the sheath 1 to support distal end actuating members (forceps cups 3a, 3b and link plates 5a, 5b) that are driven by means of the manipulating wire 2.

A slit 41 is formed in the distal end support member 4 extending from its distal end to a point close to its basal end. A support shaft 9 is provided to traverse the slit 41 in a position close to its distal end and the forceps cups 3a, 3b as well as the link plates 5a, 5b are pivotally supported on the shaft 9.

The forceps cups 3a, 3b and the link plates 5a, 5b are formed in two pairs each being a unitary assembly of one forceps cup and one link plate. Being supported on the shaft 9, the forceps cups 3a, 3b are opened and closed like a bird's beak ahead of the distal end support member 4. The link plates 5a, 5b are provided within the slit 41 and the distal end of the manipulating wire 2 is coupled to each link plate in a point close to its rear end portion.

The manipulating wire 2 is coupled to each of the link plates 5a, 5b in pair, so it actually consists of two wires in pair that are stranded together within the sheath 1 so that they can be actuated in unison. If desired, the two wires may be coupled to a single different manipulating wire within the sheath 1.

Figure 1:
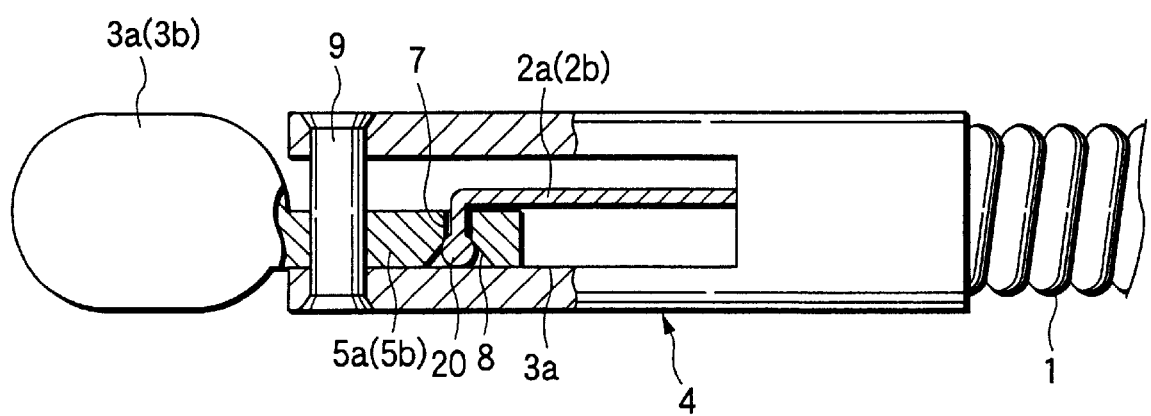
FIG. 1 is a plan view showing in partial section the distal end portion of an endoscopic biopsy forceps according to a first example of the invention.

FIG. 1 shows a coupling between one link plate 5a and the distal end portion of the associated manipulating wire 2a. Although not shown, the other link plate 5b and the associated manipulating wire 2b are positioned symmetrically with respect to the longitudinal axis of the distal end support member 4.

Each link plate 5a, 5b has an engagement hole 7 that is bored all the way through and it has a slightly larger diameter than the manipulating wire 2a, 2b. The engagement hole 7 is open as an outwardly tapered recess 8 or a recess that is flared toward the outer surface of the link plate 5a, 5b.

The manipulating wire 2a, 2b extends from the distal end of the sheath 1 and is passed through the engagement hole 7 in such a way that its distal end is situated within the recess 8. On the other hand, in the point where it projects from the other end of the engagement hole 7 (which faces the inner surface of the link plate 5a, 5b) to become exposed in the slit 41, the manipulating wire 2a, 2b is bent at generally right angles such that it extends along the inner surface of the link plate 5a, 5b toward the distal end of the sheath 1.

The distal end of the manipulating wire 2a, 2b located within the recess 8 is provided with a large-diameter portion 20 so large that it is incapable of passing through the engagement hole 7. The large-diameter portion 20 is in substantial contact with the end portion of the engagement hole 7 which is open to the bottom of the recess 8.

In the example under consideration, the large-diameter portion 20 is formed by expanding and hardening the distal end portion of the manipulating wire 2a, 2b. Stated specifically, it is formed by first melting the end portion of the strand in the manipulating wire 2a, 2b with arc, plasma or by some other suitable means until it becomes a thick enough globule and then hardening the same. During the melting, the manipulating wire 2a, 2b may be deteriorated by oxidation but this can be prevented by using an inert gas atmosphere such as argon gas.

Thus, the large-diameter portion 20 is not formed by connecting a separate component to the manipulating wire 2a, 2b but by deforming the end portion of it. Consequently, the large-diameter portion 20 retains high strength and will not come off the manipulating wire 2a, 2b even if a strong external force is applied.

The thus constructed coupling of an endoscopic treatment instrument manipulating wire according to the first example of the invention features high practical feasibility since the structure that brings the manipulating wire 2a, 2b into engagement with the associated link plate 5a, 5b can be realized by simple working and assembling operations. In addition, the structure is such that it prevents the large-diameter portion 20 from slipping out of the engagement hole 7, thereby establishing a sufficient strength in engagement to ensure that the distal end of the manipulating wire 2a, 2b will not come off either of the link plates 5a, 5b.

If desired, the large-diameter portion 20 at the distal end of the manipulating wire 2a, 2b may be formed by brazing, welding, crimping or otherwise fastening a metallic spherical section or the like to the distal end portion of the wire 2a, 2b.

Figure 3:
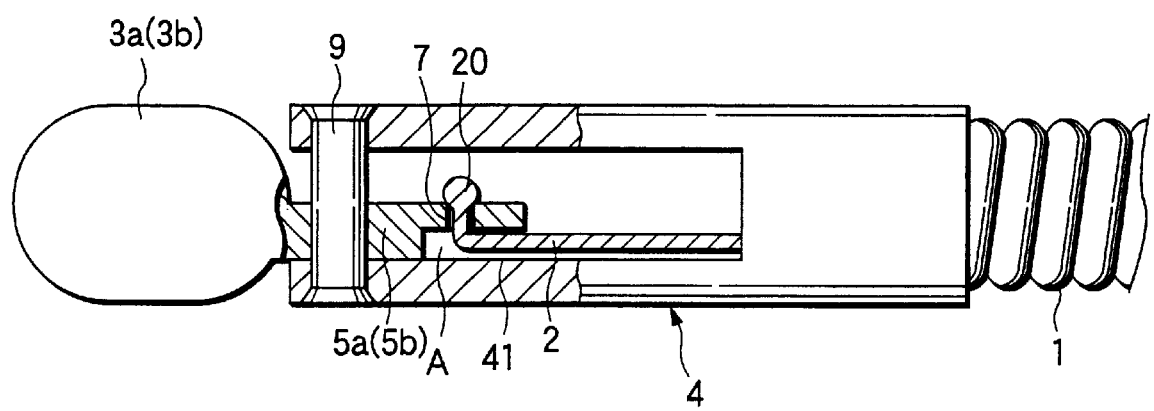
FIG. 3 is a plan view showing in partial section the distal end portion of an endoscopic biopsy forceps according to a second example of the invention.

FIG. 3 shows the coupling between the link plate 5a, 5b and the manipulating wire 2a, 2b according to the second example of the invention, in which the outer surface of the link plate 5a, 5b is skived in small thickness and the manipulating wire 2a, 2b is then placed in the space A defined by the skived outer surface of the link plate 5a, 5b and the inner sidewall of the slit 41 in the distal end support member 4 in such a way that the large-diameter portion 20 makes substantial contact with the inner surface of the link plate 5a, 5b. This design eliminates the possibility that the large-diameter portion 20 bumps against the edges of the slit 41.

Figure 4:
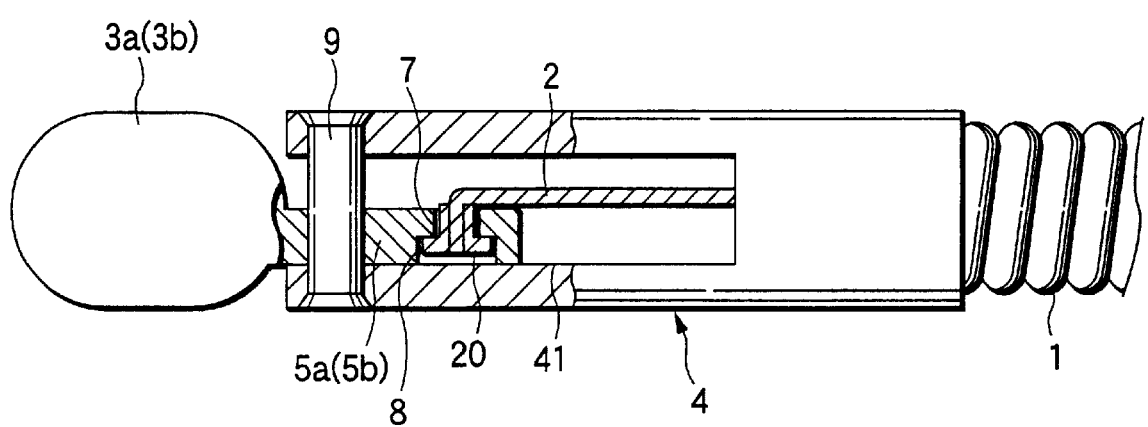
FIG. 4 is a plan view showing in partial section the distal end portion of an endoscopic biopsy forceps according to a third example of the invention.

FIG. 4 shows the coupling between the link plate 5a, 5b and the manipulating wire 2a, 2b according to the third example of the invention, in which the large-diameter portion 20 is formed by fastening a metallic flange-like member to the distal end portion of the manipulating wire 2a, 2b.

The flange-like member that forms the large-diameter portion 20 is a tubular portion that loosely fits into the engagement hole 7 and which has a flange at an end that projects in a larger diameter than the engagement hole 7 to be received in a countersunk recess 8. The other end of the flange-like member forming the large-diameter portion 20 projects beyond the other end of the engagement hole 7 to become exposed in the interior of the slit 41.

While the present invention has been described above in detail with particular reference to three examples, it should be understood that the invention may be applied to various endoscopic treatment instruments other than endoscopic biopsy forceps.

The present invention is characterized in that the distal end of the manipulating wire extending from the distal end of the sheath is provided with a large-diameter portion that is large enough to be incapable of passing through the engagement holes in the plate portions of the distal end actuating members.

The invention is also characterized in that the manipulating wire as passed through the engagement holes until the large-diameter portion contacts an end portion of each engagement hole is bent back toward the distal end of the sheath at the other end of each engagement hole.

This design offers high practical feasibility since the structure that brings the manipulating wire into engagement with the distal end actuating members can be realized by simple working and assembling operations. In addition, the structure has a sufficient strength against the loss of engagement.

Figure 5:
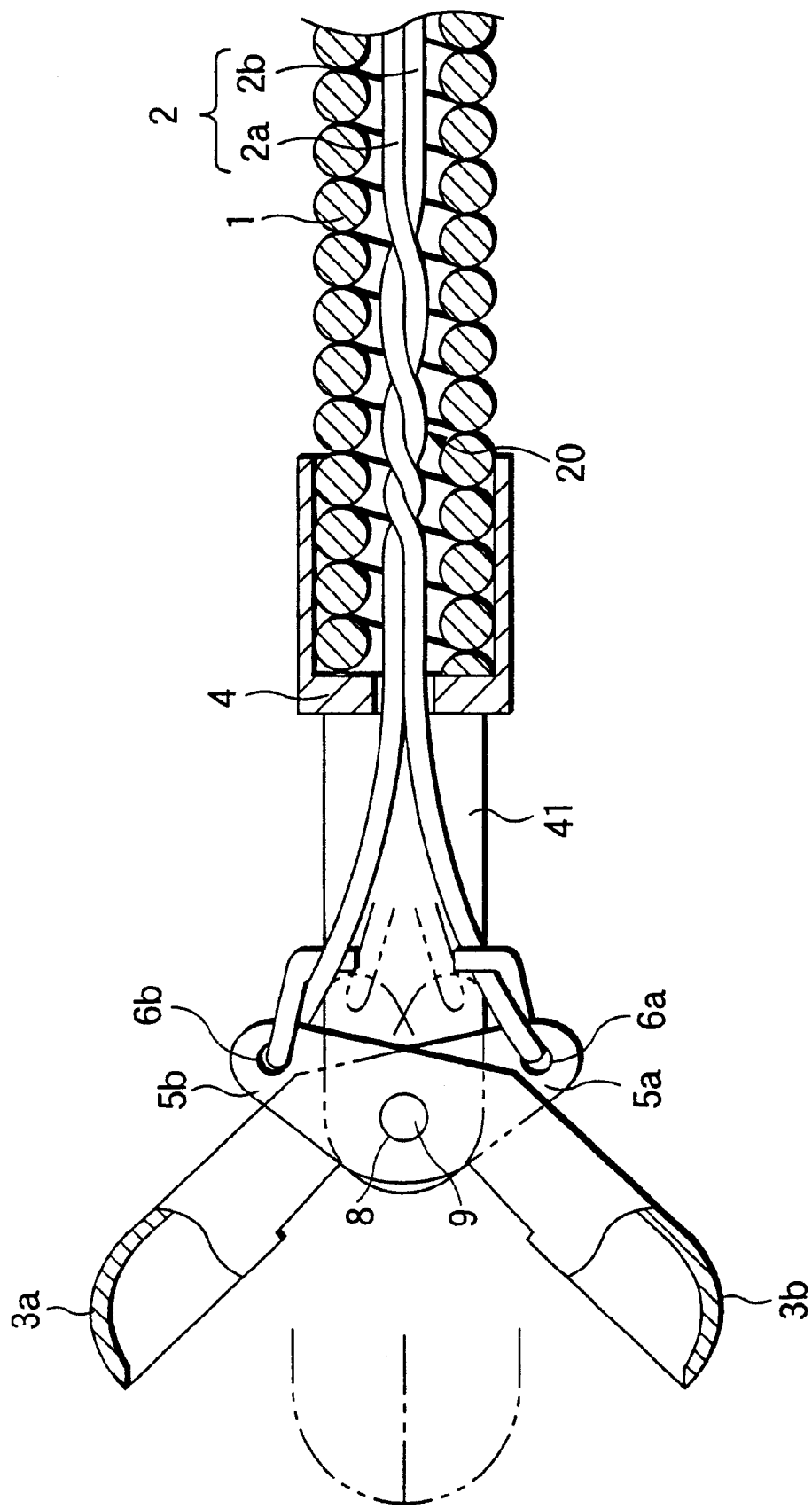
FIG. 5 is a side view showing in partial section the distal end portion of an endoscopic biopsy forceps according to a fourth example of the invention.

FIG. 5 shows the distal end portion of the flexible sheath 1 equipped with the forceps sections 3a and 3b in a fourth example of the invention. A distal end support frame 4 as securely coupled to the distal end of the flexible sheath 1 has a slit 41 formed in the front half to have a shape resembling a fork.

The pair of forceps sections 3a and 3b are integrally coupled to associated drive levers 5a and 5b, respectively. A support shaft 9 is fitted to the distal end support frame 4 in a point near the distal end such that it traverses the slit 41. The shaft 9 is passed through a hole 8 formed at the boundary between the forceps section 3a (or 3b) and the drive lever 5a (or 5b) such that the pair of forceps sections 3a and 3b pivot on the shaft 9 to open and close like a bird's beak.

Two wires 2a and 2b each consisting of a stainless steel wire or stranded stainless steel wires are arranged side by side within the flexible sheath 1 to construct the manipulating wire 2. The distal ends of the two wires 2a and 2b project forward from the distal end of the flexible sheath 1 to engage small holes 6a and 6b formed in the drive levers 5a and 5b near the rear end.

In the example under consideration, the distal end of the wire 2a, 2b passed through the small hole 6a, 6b is folded back in loop and retained onto a part of the wire 2a, 2b. Any other structure may be adopted by the engagement between wire and small hole. For example, the large-diameter portion 20 and the engagement hole 7 as discussed in connection with the first to third examples may be used to couple the distal end of the wire 2a, 2b to the drive lever 5a, 5b.

In order to ensure that the forceps sections 3a and 3b can smoothly change direction relative to the distal ends of the wires 2a and 2b, the latter should not be fixed to the small holes 6a and 6b but must be coupled rotatably.

The two wires 2a and 2b forming the manipulating wire 2 are twisted together within the flexible sheath 1 near its distal end. The twist area is indicated by 20 and it is only in this area that the wires 2a and 2b are twisted together several times in the example under consideration.

Thus, the two wires 2a and 2b are twisted together to form "a bundle". However, unlike in the related art discussed in the "Background of the Invention" section, there is no need to use any "bundling" member that increases the diameter of the manipulating wire 2 and this eliminates the need to increase the diameter of the flexible sheath 1.

Given the construction just described above, if the manipulating section 10 is operated to move the manipulating wire 2 back and forth, the drive levers 5a and 5b coupled to the distal ends of the wires 2a and 2b pivot on the support shaft 9, whereupon the forceps sections 3a and 3b open and close like a bird's beak.

Since the two wires 2a and 2b forming the manipulating wire 2 are twisted together in the twist area 20 which is in the neighborhood of its distal end, the distal end portions of the wires 2a and 2b will not move unevenly but the respective forceps sections 3a and 3b will open and close by equal degrees.

If the small holes 6a and 6b formed in the two drive levers 5a and 5b, respectively, are positionally offset by machining errors and other factors, the lengths of wires 2a and 2b extending forward from the twist area 20 may be finely adjusted to synchronize the opening and closing movements of the forceps sections 3a and 3b.

Figure 6:
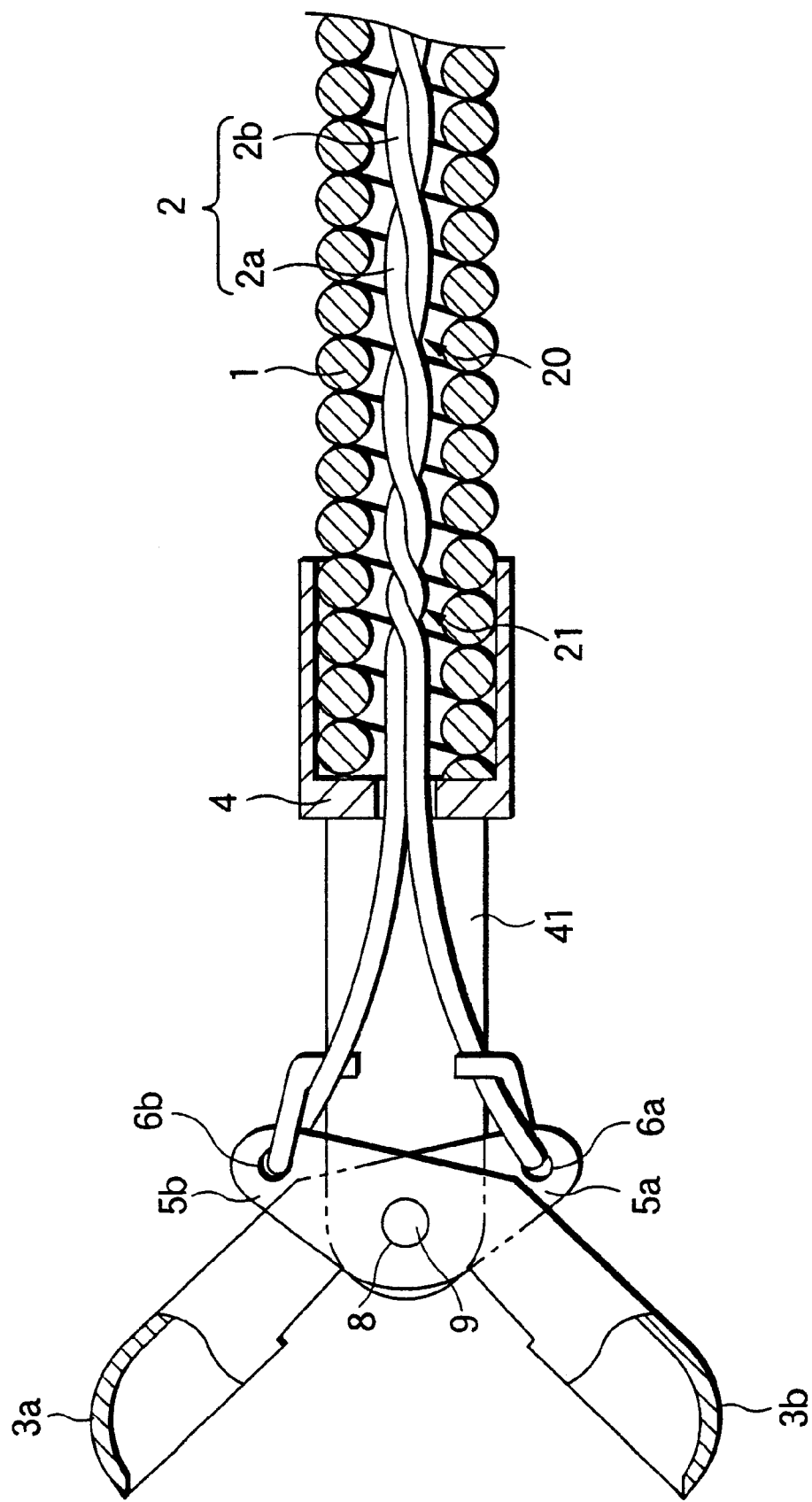
FIG. 6 is a side view showing in partial section the distal end portion of an endoscopic biopsy forceps according to a fifth example of the invention.

FIG. 6 shows the distal end portion of an endoscopic biopsy forceps according to a fifth example of the invention. The only difference from the fourth example is that the manipulating wire 2 consists of two wires 2a and 2b that are twisted together within the flexible sheath 1 in the neighborhood of its distal end and all the way backward as indicated by 20. That is, the two wires 2a and 2b are twisted together almost entirely from the support frame 4 to the manipulating section 10. This design brings about the same result as in the first embodiment.

In the fifth example, the pitch on which the two wires 2a and 2b are twisted together is smaller in the foremost end portion 21 of the twist area 20 than in the other areas, thereby allowing the two wires 2a and 2b in that foremost end portion to be bound more positively than in the other areas.

While the present invention has been described with reference to the foregoing fourth and fifth examples, it should be understood that the invention is applicable to endoscopic seizing forceps, scissors forceps and various other kinds of endoscopic forceps that can be remotely manipulated to open and close the forceps sections at the tip like a bird's beak.

The endoscopic forceps of the invention has two wires arranged side by side within a sheath to construct a manipulating wire, with the distal end of each wire being coupled to an associated drive lever, and it is characterized by twisting together the two wires within the sheath in the neighborhood of its distal end. Because of this design, the forceps sections formed integral with the drive levers can be opened and closed by equal degrees so that they accurately move as desired. In addition, this can be achieved without increasing the diameter of the sheath and, hence, the endoscopic forceps of the invention finds extensive use if it is passed through endoscopes that have built-in forceps channels of ordinary diameters.

Figure 7:
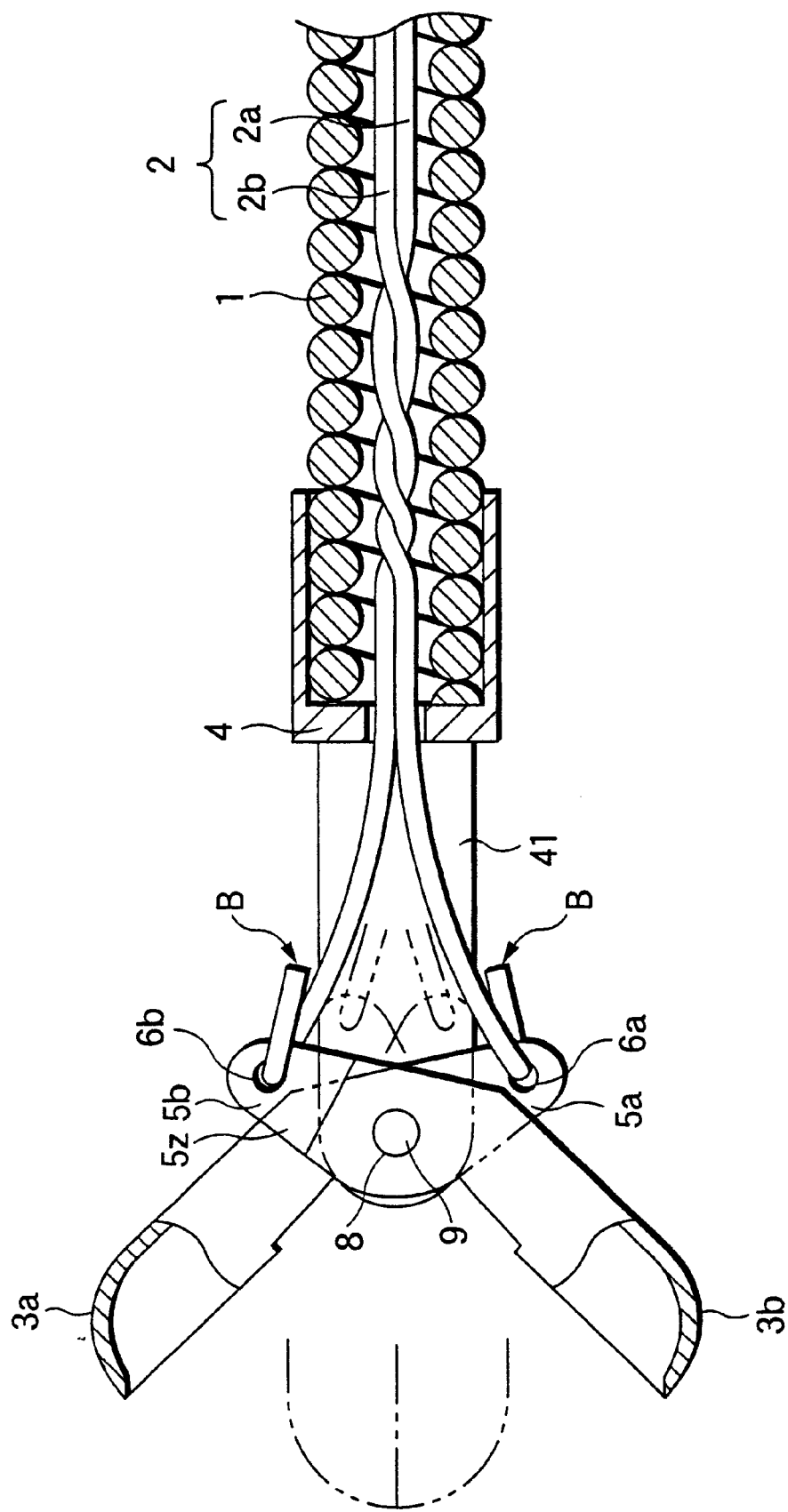
FIG. 7 is a side view showing in partial section the distal end portion of an endoscopic biopsy forceps according to a sixth example of the invention.

FIG. 7 shows an endoscopic biopsy forceps constructed according to a sixth example of the invention. A difference between the sixth example and fourth example is that the distal end of the wire 2a, 2b passed through the small hole 6a, 6b and folded back in loop is retained onto a part of the wire 2a, 2b in the fourth example, whereas the distal end of the wire 2a, 2b passed through the small hole 6a, 6b is simply foled back in the sixth example.

Figure 8:
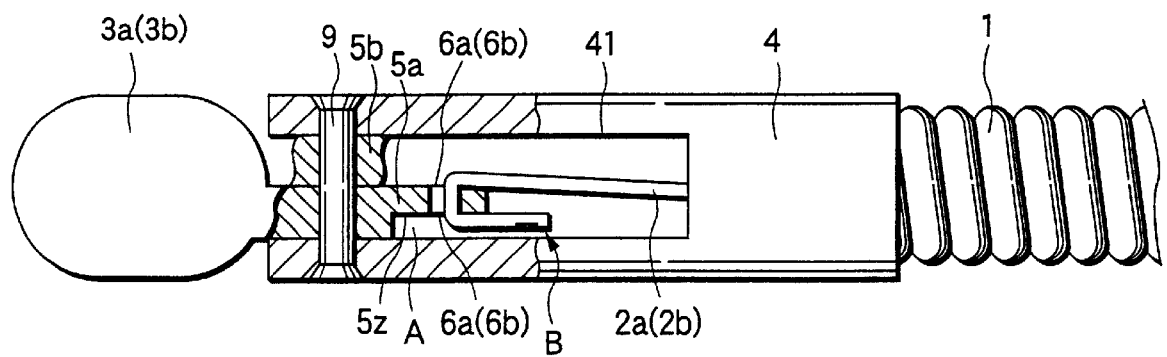
FIG. 8 is a plan view showing in partial section the distal end portion of the endoscopic biopsy forceps according to the sixth example of the invention.

In the sixth example under consideration, as shown in FIG. 8, the coupling between the distal end of the wire 2a, 2b and the associated drive lever 5a, 5b is such that the surface of the drive lever 5a, 5b which contacts the inner sidewall of the slit 41 in the area closer to the rear end is skived in such a way as to create a gap A with the inner sidewall of the slit 41. The skived surface of the drive lever 5a, 5b is indicated by 5z.

Small holes 6a and 6b are formed in the drive levers 5a and 5b in the neighborhood of their rear end. The distal end portions of the wires 2a and 2b are passed through these small holes and turned up to fit into the gap A.

Figure 9:
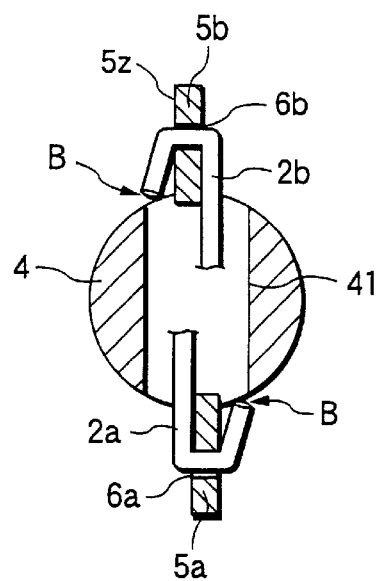
FIG. 9 is a front view showing in partial section the distal end portion of the endoscopic biopsy forceps according to the sixth example of the invention.

During repeated use of the forceps, the turn-ups of the wires 2a and 2b may deform to spread somewhat. Then, as is clear from FIG. 9 which is a front view showing in section the distal end portion of the endoscopic biopsy forceps of the sixth example, the distal end B of the turn-up of wire 2a or 2b may get stuck at the throat of the slit 41, occasionally causing failure in the operation of the forceps.

For this reason, it is preferable to employ an arrangement which will be described with reference to seventh to ninth examples of the invention.

Figure 10:
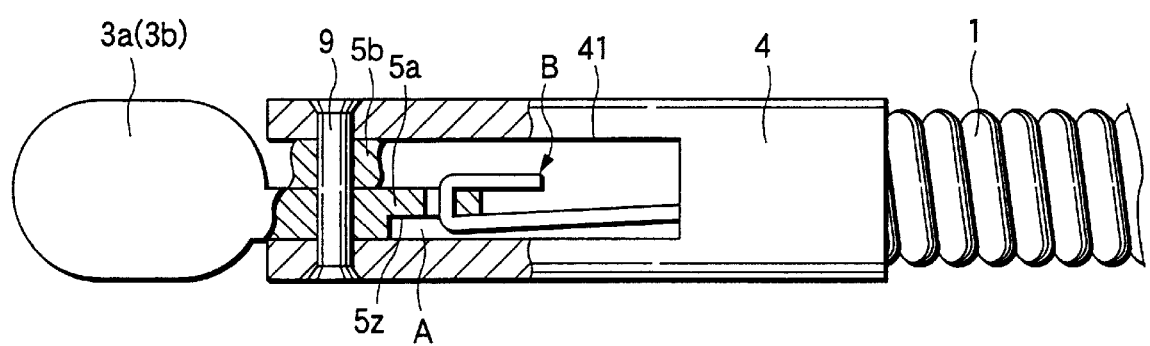
FIG. 10 is a plan view showing in partial section the distal end portion of an endoscopic biopsy forceps according to a seventh example of the invention.
Figure 11:
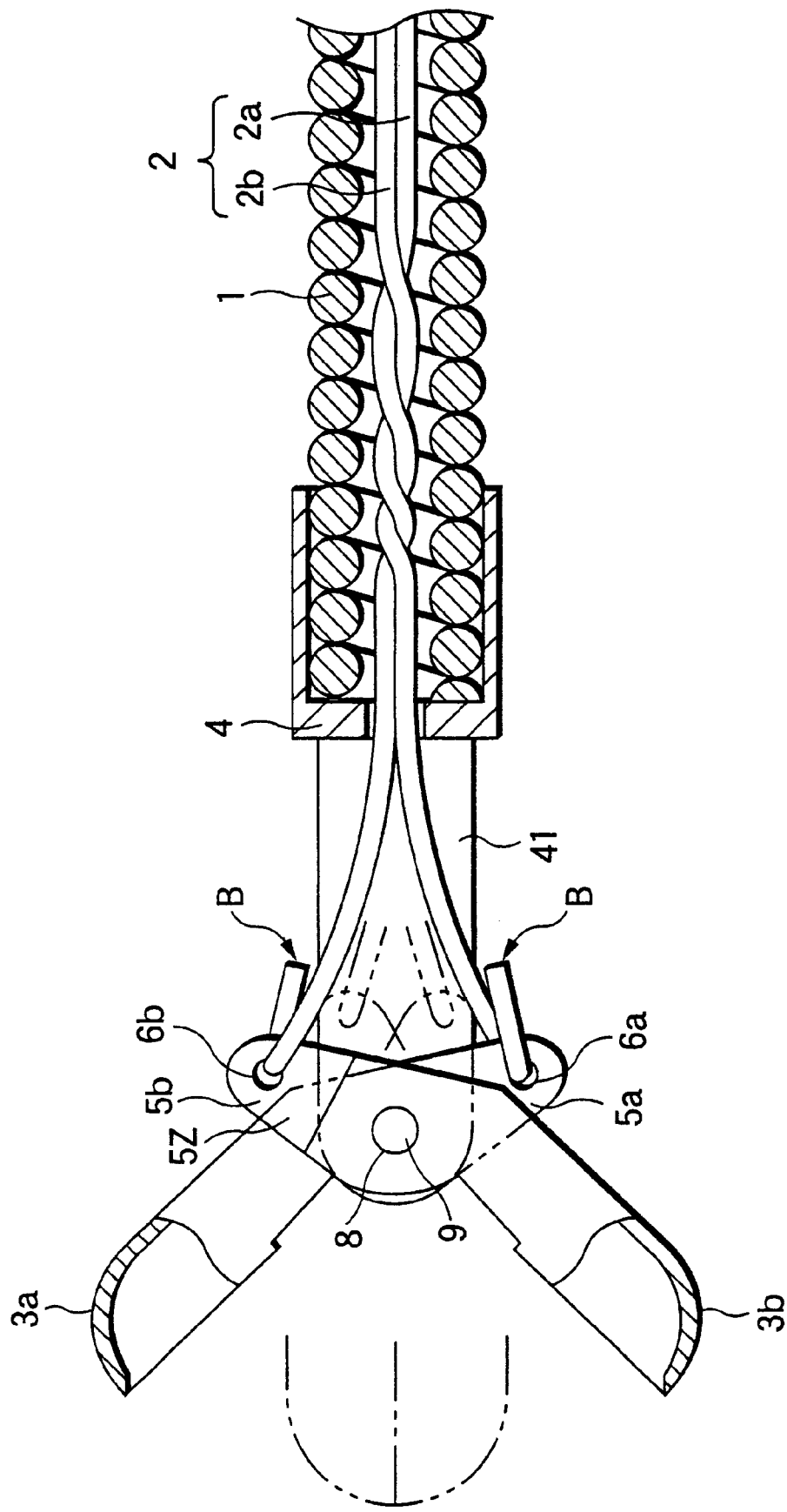
FIG. 11 is a side view showing in partial section the distal end portion of the endoscopic biopsy forceps according to the seventh example of the invention.

FIG. 10 shows an endoscopic forceps constructed according to a seventh example of the invention.

Drive levers 5a and 5b are integrally coupled to the forceps sections 3a and 3b, respectively, and sandwiched side by side within the slit 41 as shown in FIG. 10.

A support shaft 9 is fitted near the distal end of the distal end support frame 4 in such a way as to traverse the slit 41. The shaft 9 is passed through holes 8 formed in the drive levers 5a and 5b at a point closer to their distal end so that the pair of drive levers 5a and 5b are pivotally supported on the shaft 9. When the drive levers 5a and 5b pivot on the shaft 9, the pair of forceps sections 3a and 3b open and close like a bird's beak.

Two wires 2a and 2b each consisting of a stainless steel wire or stranded stainless steel wires are arranged side by side within the flexible sheath 1 to construct the manipulating wire 2. The distal end portions of the two wires 2a and 2b project forward from the distal end of the flexible sheath 1 to engage small holes 6a and 6b formed in the drive levers 5a and 5b near their rear end.

The surface of the drive lever 5a, 5b which contacts the inner sidewall of the slit 41 in the area closer to the rear end is skived in such a way as to create a gap A with the inner sidewall of the slit 41. The skived surface of the drive lever 5a, 5b is indicated by 5z. The wires 2a and 2b that extend from the sheath 1 are first pulled into the gap A, then bent toward the small holes 6a and 6b.

In the example under consideration, the end portions of the wires 2a and 2b passed through the small holes 6a and 6b are bent backward in the space whose width is one half the width of the slit 41.

In order to ensure that the forceps sections 3a and 3b can smoothly change direction relative to the distal ends of the wires 2a and 2b, the latter should not be fixed to the small holes 6a and 6b but must be coupled rotatably.

The two wires 2a and 2b 2 are twisted together within the flexible sheath 1 near its distal end to form "a bundle". Therefore, by moving the manipulating wire 2 back and forth, the two wires 2a and 2b can be uniformly moved in operative association.

Given the construction just described above, if the manipulating section 10 is operated to move the manipulating wire 2 back and forth, the drive levers 5a and 5b coupled to the distal ends of the wires 2a and 2b pivot on the support shaft 9, whereupon the forceps sections 3a and 3b open and close like a bird's beak.

Figure 12:
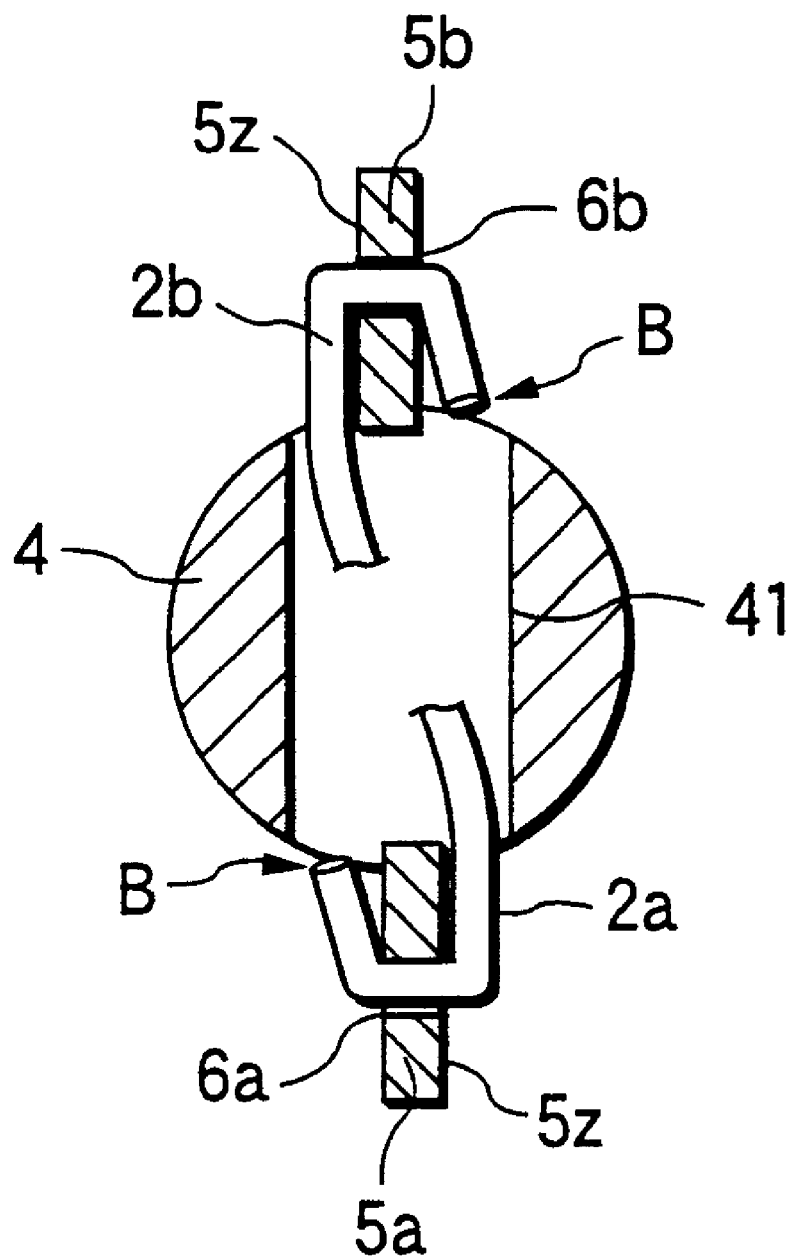
FIG. 12 is a front view showing in partial section the distal end portion of the endoscopic biopsy forceps according to the seventh example of the invention.

During these movements, the end portion B of the turned-up wire 2a, 2b goes in or comes out of the slit 41 from a lateral side. As is clear from FIG. 10 and FIG. 12 which is a front view showing the distal end of the endoscopic biopsy forceps enlarged in section, the end portion B of each wire 2a, 2b is located in the wide space whose width is one half the width of the slit 41, so even if it spreads somewhat as a result of repeated use of the forceps, it will not get stuck at the throat of the slit 41 and the forceps sections can be opened and closed in positive movements.

Figure 13:
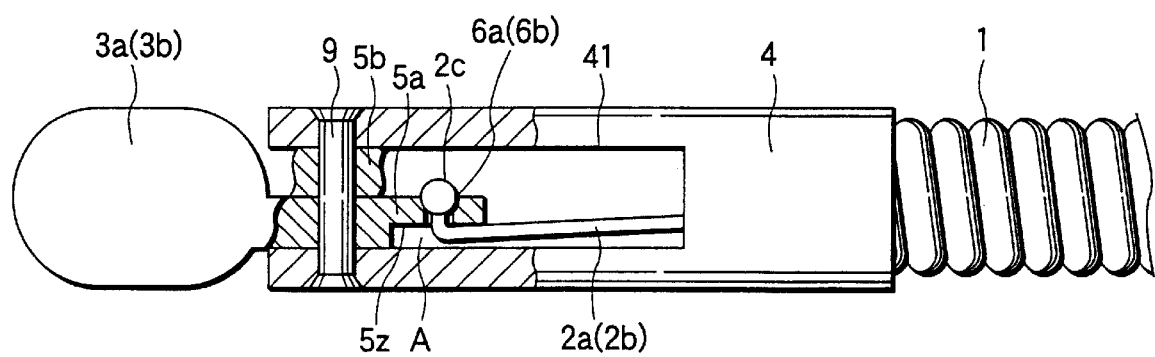
FIGS. 13 is a plan view showing in partial section the distal end portion of an endoscopic biopsy forceps according to an eighth example of the invention.

FIG. 13 shows the distal end portion of an endoscopic biopsy forceps according to an eighth example of the invention. As in the seventh embodiment, the wire 2a, 2b extending from the sheath 1 is directed into the gap A between the skived surface of the drive lever 5a, 5b and the inner sidewall of the slit 41.

In the eighth example, each of the wires 2a and 2b passing through the gap A to be bent toward the small holes 6a and 6b is provided with a spherical stopper 2c (the large-diameter portion) at the tip so that those wires will not slip out of the small holes 6a and 6b. Even with this design, the present invention prevents the stopper 2c from bumping against the throat of the slit 41 and allows the forceps sections 3a and 3b to be opened and closed in positive movements.

Figure 14:
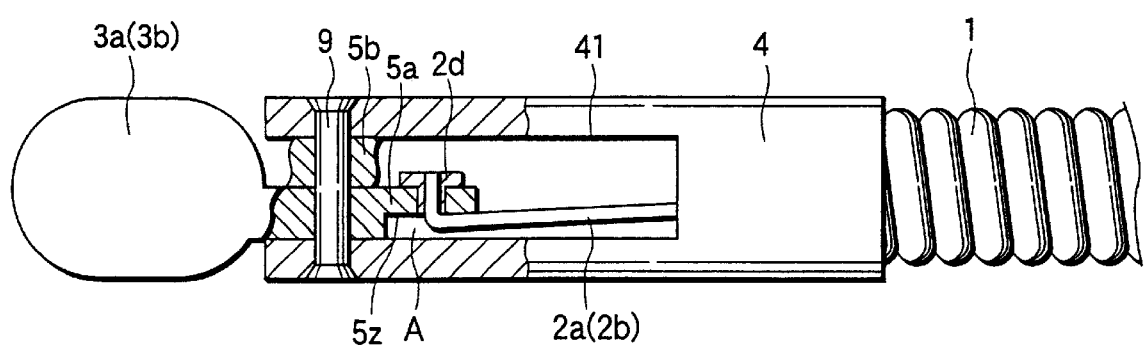
FIG. 14 is a side view showing in partial section the distal end portion of the endoscopic biopsy forceps according to a ninth example of the invention.

FIG. 14 shows the distal end portion of an endoscopic biopsy forceps according to the ninth example of the invention. As in the seventh and eighth examples, the wire 2a, 2b extending from the sheath 1 is directed into the gap A between the skived surface of the drive lever 5a, 5b and the inner sidewall of the slit 41.

In the ninth example, each of the wires 2a and 2b passing through the gap A to be bent toward the small holes 6a and 6b is provided with a stopper 2d in the form of a grommet (the large-diameter portion) at the tip so that those wires will not slip out of the small holes 6a and 6b. Even with this design, the present invention prevents the stopper 2d from bumping against the throat of the slit 41 and allows the forceps sections 3a and 3b to be opened and closed in positive movements.

Figure 15:
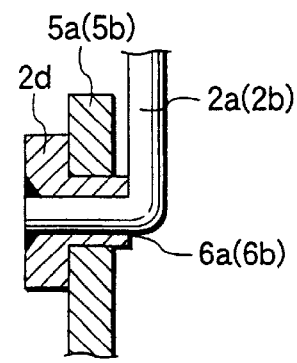
FIG. 15 is an enlarged side view showing in partial section a connecting portion between a manipulating wire and a drive lever in the distal end portion of the endoscopic biopsy forceps according to the ninth example of the invention.

As shown enlarged in FIG. 15, if the small-diameter portion of the stopper 2d passing through the small hole 6a or 6b is designed to be longer than these small holes, the wires 2a and 2b will not have direct contact with the drive levers 5a and 5b but have smoother movements in opening and closing the forceps sections 3a and 3b.

While the present invention has been described with reference to the foregoing examples, it should be understood that the invention is applicable to endoscopic seizing forceps, scissors forceps and various other kinds of endoscopic forceps that can be remotely manipulated to open and close the forceps sections at the tip like a bird's beak.

In the endoscopic forceps of the invention, the surface of each of two drive levers which contacts the inner sidewall of a slit in the area closer to the rear end is skived in such a way as to create a gap with the inner sidewall of the slit and a wire extending from the tip of a sheath is pulled into the gap and coupled to the associated drive lever. As a result, the end of each wire is located in a wide space whose width is one half the width of the slit and even if it deforms to spread somewhat, the wires will not get stuck at the throat of the slit and allow the forceps cups to be opened and closed in positive movements.

Figure 16:
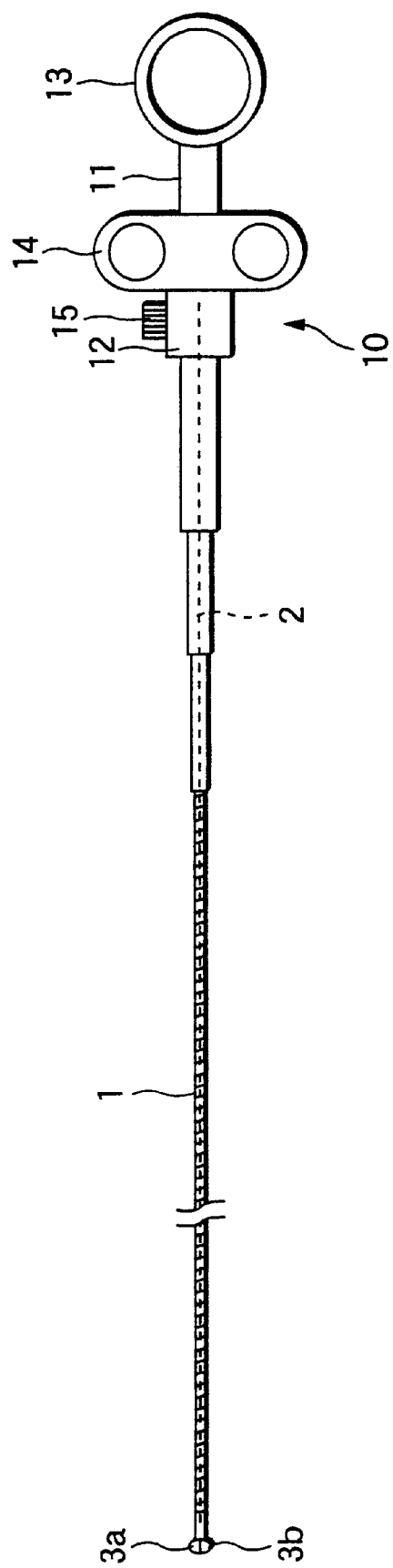
FIG. 16 shows an entire structure of an endoscopic biopsy forceps according to the present invention.

FIG. 16 shows an entire view of an endoscopic forceps that is an example of an endoscopic treatment instruments to which each of the structures described with reference to the first to ninth examples is applicable. As illustrated, a manipulating section 10 for allowing the manipulating wire 2 to be moved back and forth is coupled to the basal end portion of the flexible sheath 1 which is closer to the operator. The manipulating section 10 comprises a body 11 and a slider 12 that can be relatively moved back and forth along the longitudinal axis and they are relatively fitted with pull rings 13 and 14. The basal end of the manipulating wire 2 is coupled to the slider 12 by means of a manual fastening screw 15.

Figure 17:
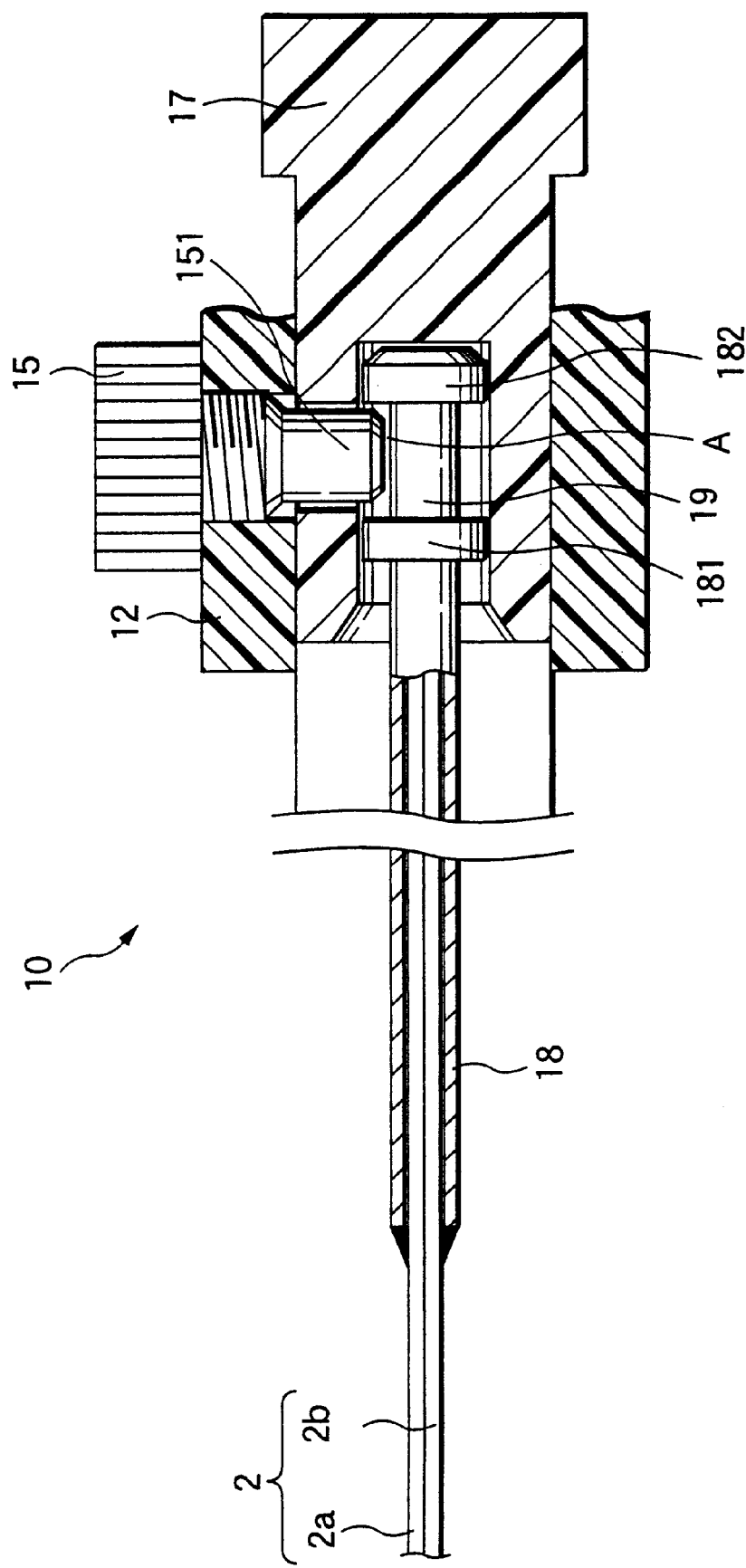
FIG. 17 shows, in partial section, a manipulating portion of the endoscopic biopsy forceps according to the present invention.

FIG. 17 shows the structure for fixing the basal end portion of the manipulating wire 2 in the manipulating section 10.

As shown, the basal ends of the two wires 2a and 2b are securely inserted into a single bundling pipe 18 and a pair of flanges 181 and 182 spaced apart along the longitudinal axis are provided in the basal end portion of the bundling pipe 18.

That part of the bundling pipe 18 where the flanges 181 and 182 are formed is loosely inserted into a hole formed through the longitudinal axis of a pipe receiving member 17 fitted into the slider 12. The fastening screw 15 that threadably engages the slider 12 from a lateral side has a rod-like portion 151 formed in its distal end portion; the rod-like portion 151 penetrates the wall of the pipe receiving member 17 to come into the space between the flanges 181 and 182 so that the bundling pipe 18 can move along the longitudinal axis together with the slider 12.

The distal end face of the rod-like portion 151 of the fastening screw 15 does not touch the bundling pipe 18 but is spaced from it by a gap A. Hence, the bundling pipe 18 and the manipulating wire 2 coupled to it are rotatable on the longitudinal axis.

As a result, deflections and other deformations of the flexible sheath 1 will not develop any force to rotate the manipulating wire 2, so that the distal end portions of the wires 2a and 2b will not twist relative to the small holes 6a and 6b and the forceps sections 3a and 3b can always be driven to open and close smoothly.

What is claimed is:

1. An endoscopic treatment instrument comprising:
   a sheath having a longitudinal axis;
   a manipulating wire passed through the sheath and movable back and forth along the longitudinal axis;
   a distal end actuating member disposed at a distal end of the sheath and driven by the manipulating wire;
   a first engagement hole provided in a plate portion of the distal end actuating member;
   a second engagement hole provided in the plate portion of the distal end actuating member, the second engagement hole being contiguous with the first engagement hole and including a portion having a larger diameter than the first engagement hole; and
   a large-diameter portion that is provided on a distal end of the manipulating wire and that is large enough to be incapable of passing through the first engagement hole, wherein the manipulating wire is passed through the first and second engagement holes until the large-diameter portion enters and remains within the second engagement hole and contacts one end portion of the first engagement hole without entering the first engagement hole and is bent back t war the distal end of said sheath at the other end of the first engagement hole.

2. The endoscopic treatment instrument according to claim 1, wherein the large-diameter portion is formed by expanding the distal end of the manipulating wire and hardening the distal end thus expanded.

3. The endoscopic treatment instrument according to claim 2, wherein the large-diameter portion is formed by expanding the distal end of the manipulating wire, melting the thus expanded distal end and then hardening the thus molten distal end.

4. The endoscopic treatment instrument according to claim 1, wherein the large-diameter portion is formed by fastening a spherical piece to the distal end of the manipulating wire.

5. The endoscopic treatment instrument according to claim 1, wherein the large-diameter portion is formed by fastening a flange member to the distal end of the manipulating wire.

6. The endoscopic treatment instrument according to claim 1, wherein the manipulating wire is twisted with another manipulating wire at least in the vicinity of the distal end of the distal end of the sheath.

7. The endoscopic treatment instrument according to claim 1, wherein the one end of the first engagement hole is located closer to the longitudinal axis of the sheath than the other end of the first engagement hole is located.

8. The endoscopic treatment instrument according to claim 7, further comprising:
   a support frame having a slit and movably supporting the distal end actuating member,
   wherein the other end of the first engagement hole is spaced from an inner sidewall of the slit.

9. An endoscopic treatment instrument comprising:
   a sheath having a longitudinal axis;
   a pair of manipulating wires passed through the sheath and movable back and forth along the longitudinal axis; and
   a pair of distal end actuating members disposed at a distal end of the sheath and connected respectively to the manipulating wires;
   wherein the manipulating wires are helically twisted around each other within the sheath at least in the vicinity of the distal end of the sheath.

10. The endoscopic treatment instrument according to claim 9, wherein the manipulating wires are helically twisted around each other only in the vicinity of the distal end of the sheath.

11. The endoscopic treatment instrument according to claim 9, wherein the manipulating wires are helically twisted around each other substantially entirely from the vicinity of the distal end of the sheath to a basal end of the sheath.

12. The endoscopic treatment instrument according to claim 11, wherein a pitch on which the manipulating wires are helically twisted is smaller in a foremost end portion of a twist area than in other areas.

13. The endoscopic treatment instrument according to claim 9, further comprising:
   a support frame having a slit and movably supporting the distal end actuating members,
   wherein each of the distal end actuating members has a skived portion at a rear end portion to define a space from an inner side wall of the slit, and wherein a part of each of the manipulating wires, which extends from a corresponding distal end actuating member to the distal end of the sheath, is located within a corresponding space.

14. The endoscopic treatment instrument according to claim 13, wherein the part of each manipulating wire is passed through the corresponding space from the distal end of the sheath, and then connected to the corresponding actuating member.

15. The endoscopic treatment instrument according to claim 9, wherein each of the actuating members includes a plate portion with an engagement hole provided therein, a distal end of each of the manipulating wires includes a large-diameter portion that is large enough to be incapable of passing through the engagement hole, and each manipulating wire is passed through an engagement hole until the large-diameter portion contacts one end portion of the engagement hole, and is bent back toward the distal end of said sheath at the other end of the engagement hole.

16. An endoscopic treatment instrument comprising:
a sheath having a longitudinal axis;
a manipulating wire passed through the sheath and movable back and forth along the longitudinal axis;
a distal end actuating member disposed at a distal end of the sheath and driven by the manipulating wire;
a support frame movably supporting the distal end actuating member, and having a slit defining an inner sidewall; and
a skived portion provided to a rear end of the actuating ember to define a space from the inner side wall which is open at the rear end,
wherein the manipulating wire extends from the distal end of the sheath and is connected to the actuating member, with a distal end of the manipulating wire disposed in the space defined by the skived portion of the actuating member and terminating prior to the distal end of the sheath.

17. An endoscopic treatment instrument comprising:
a sheath having a longitudinal axis;
a pair of manipulating wires passed through the sheath and movable back and forth along the longitudinal axis; and
a pair of distal end actuating members disposed at a distal end of the sheath and connected respectively to the manipulating wires;
wherein the manipulating wires are twisted with each other within the sheath in the vicinity of the distal end of the sheath, and substantially entirely from the vicinity of the distal end of the sheath to a basal end of the sheath.

18. The endoscopic treatment instrument according to claim 17, wherein a pitch on which the manipulating wires are twisted is smaller in a foremost end portion of a twist area than in other areas.

* * * * *